US012797152B2

(12) United States Patent
Davidner et al.

(10) Patent No.: US 12,797,152 B2
(45) **Date of Patent: *Nov. 17, 2026**

(54) DEVICES AND METHODS FOR REDUCING INTRAOPERATIVE BONE FRACTURES

(71) Applicant: OrthoIQ, LLC, Claremont, CA (US)

(72) Inventors: Alan Aaron Davidner, Claremont, CA (US); Phillip Ormond Merritt, La Canada, CA (US); Kimberly Elasky, Westlake Village, CA (US); Sean Kepler, Irvine, CA (US)

(73) Assignee: OrthoIQ, Inc., Claremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/418,451

(22) Filed: Dec. 12, 2025

(65) Prior Publication Data

US 2026/0102221 A1 Apr. 16, 2026

Related U.S. Application Data

(63) Continuation of application No. 18/337,870, filed on Jun. 20, 2023, now Pat. No. 12,514,668.

(60) Provisional application No. 63/354,207, filed on Jun. 21, 2022.

(51) Int. Cl.
*A61F 2/36* (2006.01)
*A61B 90/00* (2016.01)

(52) U.S. Cl.
CPC .............. *A61B 90/08* (2016.02); *A61B 90/37* (2016.02); *A61F 2/3609* (2013.01); *A61B 2090/0808* (2016.02)

(58) Field of Classification Search
CPC .......................... A61F 2/36–2002/3698; A61F 2/40–2002/4096
See application file for complete search history.

(56) References Cited

U.S. PATENT DOCUMENTS

| | | | | |
|---|---|---|---|---|
| 5,569,260 | A | 10/1996 | Petersen | |
| 8,118,815 | B2 | 2/2012 | van der Walt | |
| 8,974,468 | B2 | 3/2015 | Borja | |
| 9,173,661 | B2 | 11/2015 | Metzger et al. | |
| 10,251,663 | B2 * | 4/2019 | Behzadi ............... | A61B 17/142 |
| 10,363,149 | B2 * | 7/2019 | van der Walt ..... | A61B 17/1746 |
| 10,441,244 | B2 | 10/2019 | Behzadi | |

(Continued)

FOREIGN PATENT DOCUMENTS

WO 2015144129 A1 10/2015

OTHER PUBLICATIONS

Ferretti et al. article titled "The Accuracy of Patient-Specific Instrumentation with Laser Guidance in a Dynamic Total Hip Arthroplasty: A Radiological Evaluation," Sensors 2021, 21, 4232, https://doi.org/10.3390/s21124232 13 pages).

(Continued)

*Primary Examiner* — Zade Coley
(74) *Attorney, Agent, or Firm* — Aurora Consulting LLC; Albert Du; Ashley Sloat

(57) ABSTRACT

Described herein are devices and related methods configured to establish that a femoral or humerus component implant is fully seated during femoral or humerus implant impaction. Such devices described herein may include a laser, detector, and processor and, optionally, a camera. Results of the device use may be transmitted to and/or displayed on a computing device.

17 Claims, 8 Drawing Sheets

(56) References Cited

U.S. PATENT DOCUMENTS

| | | | | |
|---|---|---|---|---|
| 10,918,499 | B2 | 2/2021 | Nielsen et al. | |
| 11,058,441 | B2 | 7/2021 | Grinnell | |
| 11,426,243 | B2 * | 8/2022 | Beck | A61B 34/30 |
| 12,201,380 | B2 * | 1/2025 | Signoretti | A61F 2/46 |
| 2005/0070897 | A1 * | 3/2005 | Petersen | A61B 17/155 606/53 |
| 2007/0073296 | A1 | 3/2007 | Panchbhavi | |
| 2009/0234360 | A1 * | 9/2009 | Alexander | A61B 17/15 606/88 |
| 2010/0076505 | A1 * | 3/2010 | Borja | A61F 2/4657 606/86 R |
| 2014/0188240 | A1 | 7/2014 | Lang et al. | |
| 2018/0193171 | A1 * | 7/2018 | van der Walt | A61F 2/4684 |
| 2021/0059769 | A1 | 3/2021 | Barmes et al. | |
| 2021/0186454 | A1 | 6/2021 | Behzadi et al. | |
| 2023/0149185 | A1 | 5/2023 | Nielsen et al. | |

OTHER PUBLICATIONS

Fujii et al. article titled "Improving MiniHip femoral prosthesis positioning using a cross-laser projection system in total hip arthroplasty by an anterolateral supine approach," Int J Med Robot, 2021:17: e2214, https://doi.org/10.1002/rcs.2214 (7 pages).

Michel et al. article entitled "Monitoring the press-fit insertion of an acetabular cup by impact measurements: influence of bone abrasion," Proc Inst Mech Eng H., Oct. 2014;228(10):1027-34. doi: 10.1177/0954411914552433. Epub Sep. 25, 2014, PMID: 25258009 DOI: 10.1177/0954411914552433.

Tijou et al. article titled "Ex Vivo Evaluation of Cementless Acetabular Cup Stability Using Impact Analyses with a Hammer Instrumented with Strain Sensors," Sensors 2018, 18, 62; doi:10.3390/s18010062, www.mdpi.com/journal/sensors (13 pages).

* cited by examiner

DEVICES AND METHODS FOR REDUCING INTRAOPERATIVE BONE FRACTURES

CROSS-REFERENCE TO RELATED APPLICATIONS

This application is a continuation of U.S. Nonprovisional patent application Ser. No. 18/337,870, filed Jun. 20, 2023, which claims the priority benefit of U.S. Provisional Patent Application Ser. No. 63/354,207, filed Jun. 21, 2022, the contents of each of which are herein incorporated by reference in their entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of orthopedic surgery, and more specifically to the field of bone surgery (for example, hip and shoulder arthroplasty). Described herein are devices and methods for reducing intraoperative fractures during surgery, for example in hip and shoulder arthroplasty.

BACKGROUND

Primary Total Hip Arthroplasty (THA) procedures continue to increase. The frequency of THA procedures is expected to grow to 635,000 procedures by the year 2030. Over the years, THA has the highest satisfactory yield of any Medicare procedure performed. The procedure relieves pain and improves motion with little to no down time. THA is usually a proven, safe, and effective procedure with very few complications. When complications do arise, they are very serious requiring revision hip surgery which can cost upwards of $73,500 and may necessitate long hospital stays with serious co-morbidities. Complications occur at a 3.5% rate and include instability/dislocation and especially periprosthetic (fractures that occur around and as a result of an implant) femur fractures.

Additionally, Total Shoulder Arthroplasty (TSA) procedures also continue to increase. The frequency of TSA procedures is expected to grow to 173,000 procedures by the year 2025. New surgical procedures have also improved the outcomes of shoulder arthroplasty. Like THA, TSA has equivalent complications. When complications arise, then humerus instability/dislocation and especially periprosthetic fractures can occur.

Accordingly, new solutions are needed for preventing peri-prosthetic bone fractures and improving surgery outcomes.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

Figure 1A:
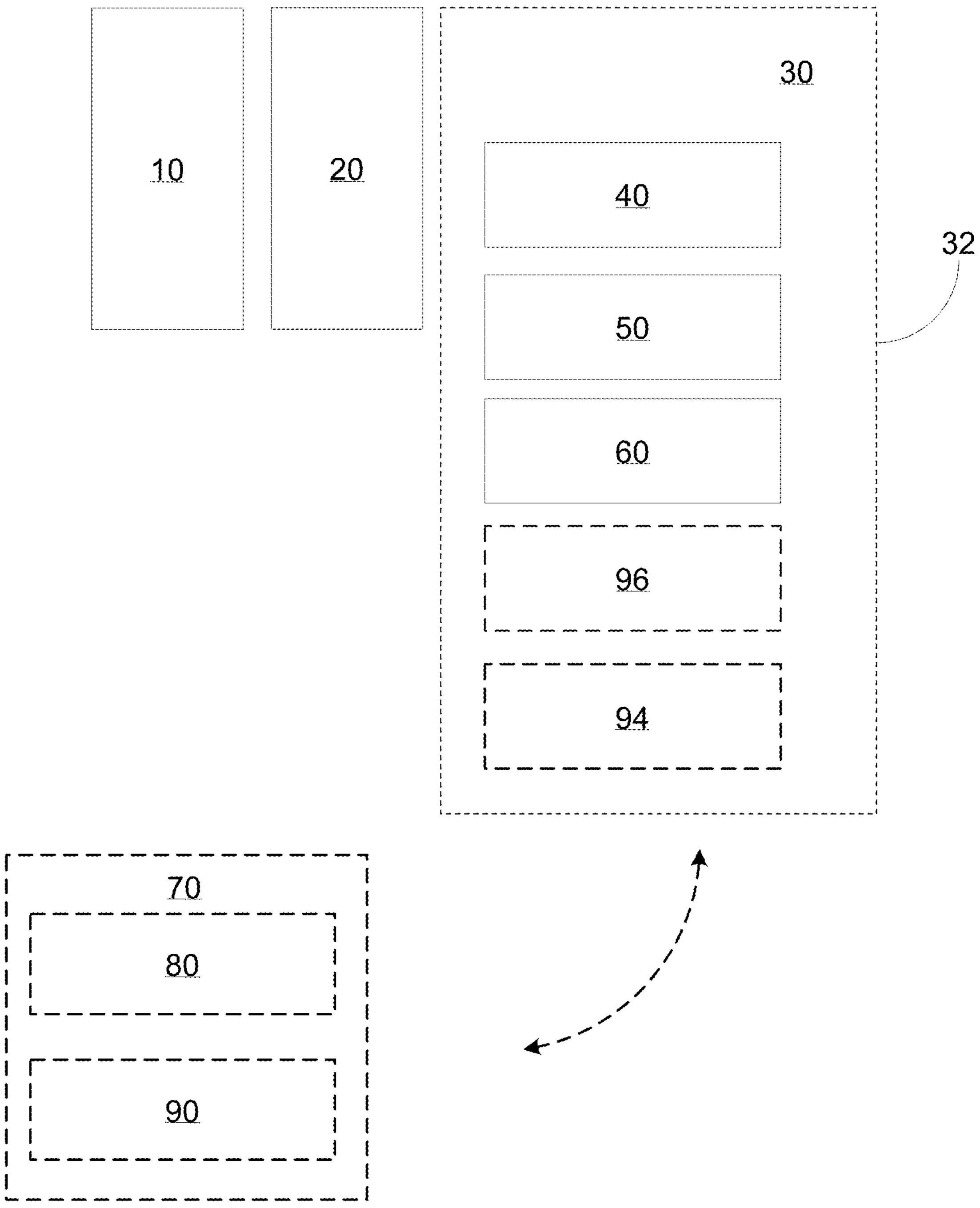
FIG. 1A shows a schematic of an embodiment of a device for monitoring fixation and stabilization during impaction of an orthopedic implement into a bone.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

New minimally invasive surgical techniques in THA offer advantages over older hip surgical approaches. The minimal surgical approaches require smaller incisions compared to older techniques and, therefore, provide a number of advantages including shorter hospital stays, less blood loss, easier rehabilitation, and faster recovery along with less pain.

However, minimally invasive surgical techniques diminish the surgeon's ability to adequately visualize anatomical structures in the surgical space, for example a proximal femur in THA. The surgeon can rely on tactile, visual, and auditory senses, but these can be subjective.

In general, THA procedures are performed by making an incision over the hip, cutting and removing the femoral head, and reaming the acetabulum (the hip socket where the femoral head rests) for the acetabular implant component. The femur is prepared with broaches and reamers or both. Innovations around preparation and installation of orthopedic implements (e.g., a femoral implant (stem) and/or broach) are described herein. As used herein, "orthopedic implement" may include a stem, an implant, an inserter, a broach, and the like.

Stress fractures can occur during the broaching/reaming of the femoral medullary canal (THA) or the humerus medullary canal (TSA) or during the installation of a stem using a surgical mallet and/or automatic impactor. The stress fractures cannot be seen in plain view or on an x-ray. Devices and methods for preventing peri-prosthetic bone fractures are described herein.

Although THA and TSA are primarily described herein, one of skill in the art will appreciate that the devices and methods described herein may be used for any orthopedic surgery where impaction and/or fixation of an orthopedic implement may be performed.

In particular, devices and related methods described herein include a diagnostic tool that is used to establish that an orthopedic implement is fully seated in a bone during orthopedic implement impaction.

Earlier approaches utilized vibration analysis (resonance) and modal analysis to establish that a stem was fully seated in the femur. The results were inconclusive and only partially predictable for hip surgery. There are too many bone quality variables and over 400 different stems worldwide. A predictive tool, with so many variables, creates clinical trial difficulties and ambiguities. Additionally, these approaches tend to include indirect measurements.

Figure 1B:
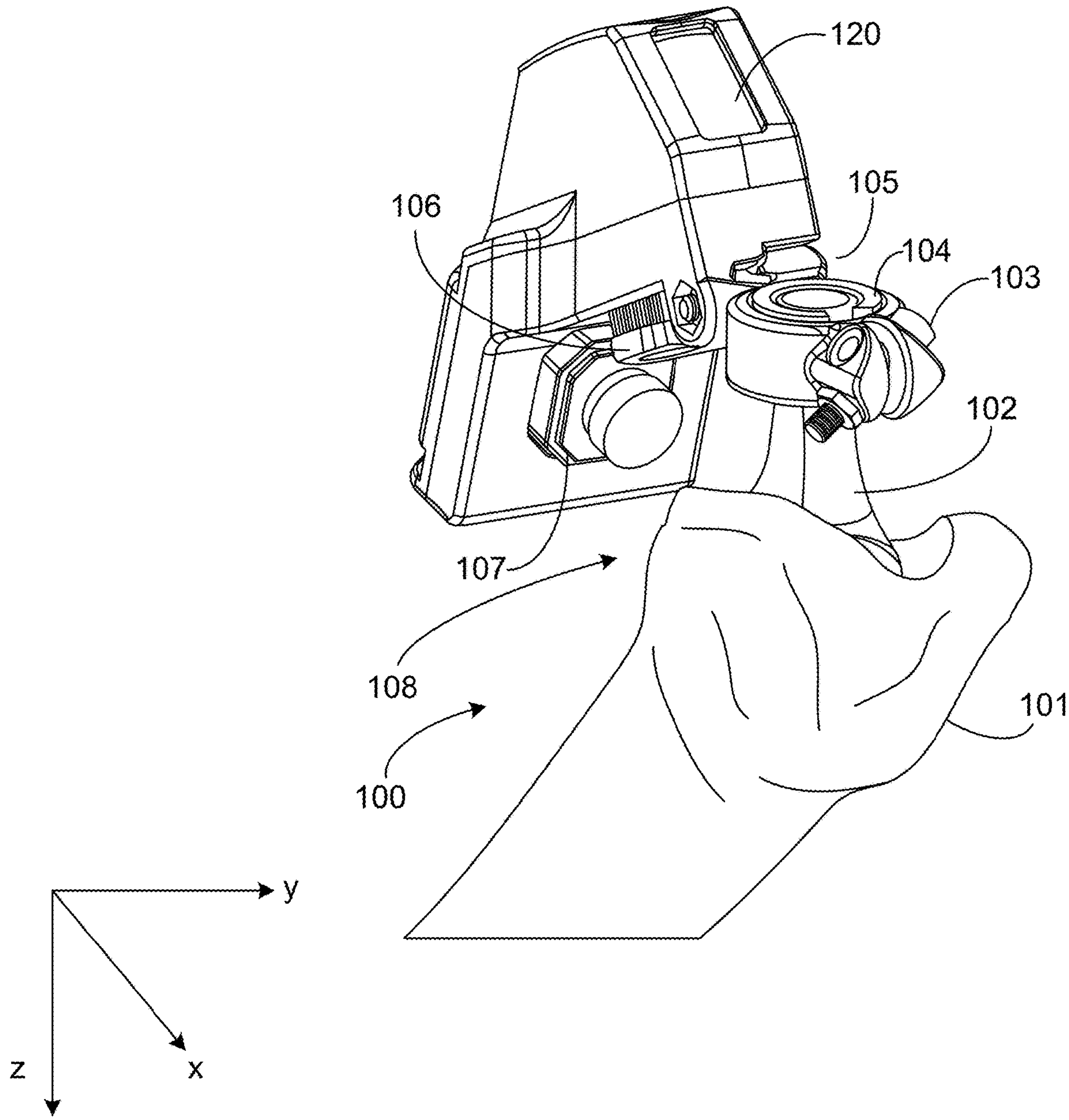
FIGS. 1B-1C show an embodiment of a device for monitoring fixation and stabilization during impaction of an orthopedic implement into a bone.
Figure 1C:
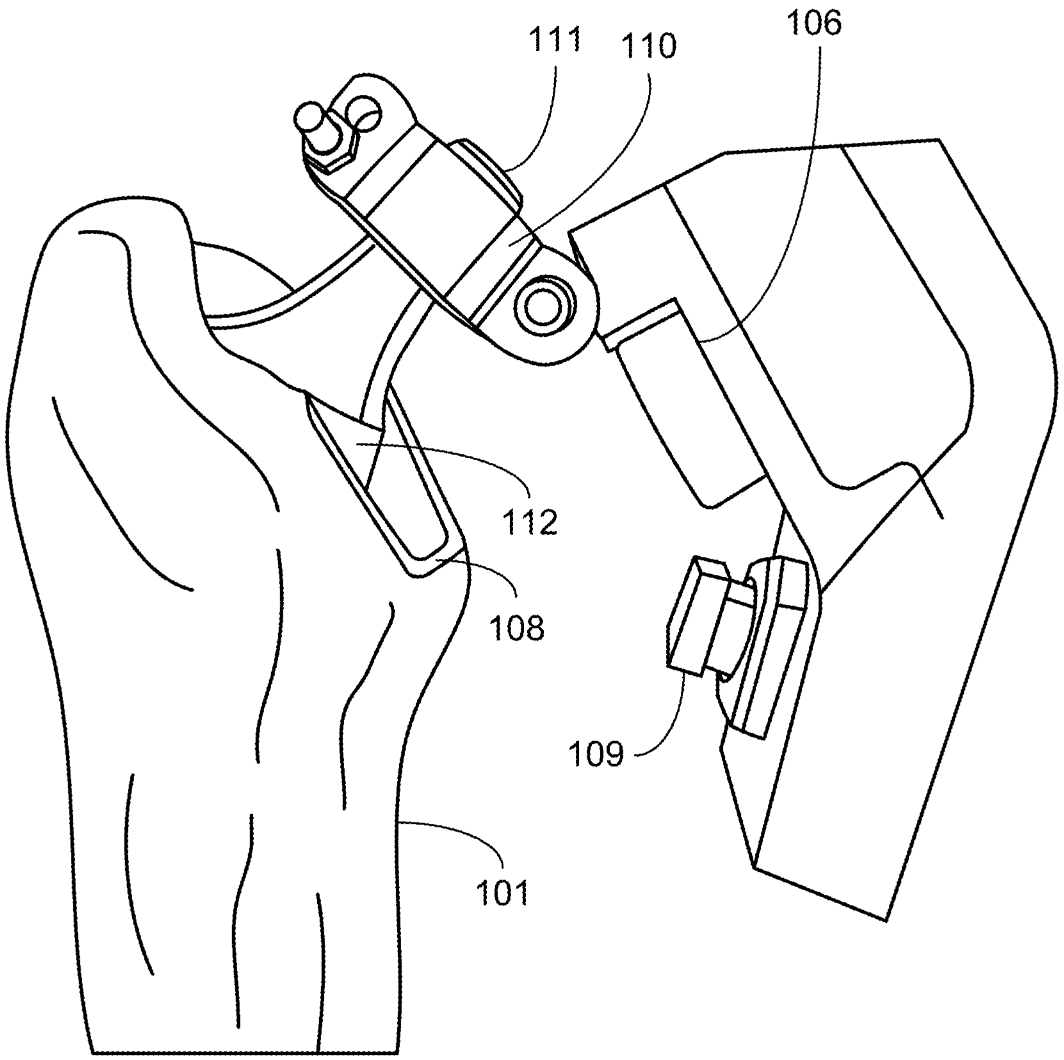

In some embodiments, as shown in FIG. 1A, the devices 30 described herein utilize a light source 40 (e.g., laser) and a detector 50 (e.g., sensor, camera, etc.) to establish the cessation of motion between an orthopedic implement 20 (e.g., here shown as an implant) and a bone 10 by accurately measuring distance (e.g., within about 2 microns to about 50 microns). In some embodiments, light source 40 and detector 50 may be a triangulating laser, such that the light source 40 and the detector 50 are a unit. The device 30 is coupled to the orthopedic implement 20, as shown in FIGS. 1A-1C. As the orthopedic implement 20 is advanced into the bone 10 (e.g., femur or humerus), for example through applied force (e.g., mallet strikes by the surgeon), the distance from the light source 40 to the cortical rim (e.g., of the femur) or cut surface of the bone changes, which is detected by a detector 50 and determined by a processor 60. The change in distance stops or exceeds or falls under a predefined threshold when the orthopedic implement 20 is fully seated or fixed within the bone 10. The surgeon can decide to stop applying force to the orthopedic implement 20 when the distance doesn't substantially change or exceeds or falls under a predetermined threshold. This approach is a direct measurement.

Device 30 may be optionally communicatively coupled to optional computing device 70. Optional computing device 70 may include an optional processor 80 and optional display 90. The distance information may be available to a user (e.g., surgeon, tech, nurse, etc.) through a user interface presented on optional display 90. In some embodiments, the distance information may be presented as a report, a graph, or other. Optional computing device 70 may be a mobile computing device, laptop, desktop computer, a television display, a heads-up display (e.g., helmet, glasses, or face shield), or the like. In some embodiments, device 30 includes an optional display 96 for displaying information, data, results, etc. on the device 30 itself. As shown in FIG. 1A, two processors are shown. Although two processors are shown, one of skill in the art may appreciate that any number of processors (e.g., one, more than one, one or more, a plurality, etc.) may be used in device 30 and/or computing device 70 or as part of a system including device 30. Further, one of skill in the art may appreciate that a subset of operations may be performed by processor 60 while other or a second subset of operations can be performed by processor 80. In some embodiments, all operations are performed by processor 60. In some embodiments, all operations are performed by processor 80.

A device 30 for measuring seating of an orthopedic implement may include detectors 50 such as a complementary metal-oxide semiconductor (CMOS) detector and light sources 40 such as a red solid-state laser as a light source, for example. The laser 106 shown in FIGS. 1A-1B may have an accuracy of about 10 microns to about 50 microns. The light beam (e.g., a pinpoint, a small oval, a line) is configured to be projected on a target on a bone (e.g., the cortical rim) under measurement at a certain incidence angle. Part of the reflected beam is trained on the focusing optics and then onto a detector 50 (e.g., CMOS) and processed by one or more processors, 60, 80 (e.g., on a chip). As the orthopedic implement is advanced into the bone (e.g., femur or humerus), the light beam shifts on the target (e.g., cortical rim) and the reflected angle of the light beam changes causing the light to move across the detector 50. Because the incident light and reflected light form a triangle, the Pythagoras theorem may be used by one or more processors 60, 80 to calculate or determine the light spot displacement, and thus a distance.

Figure 5:
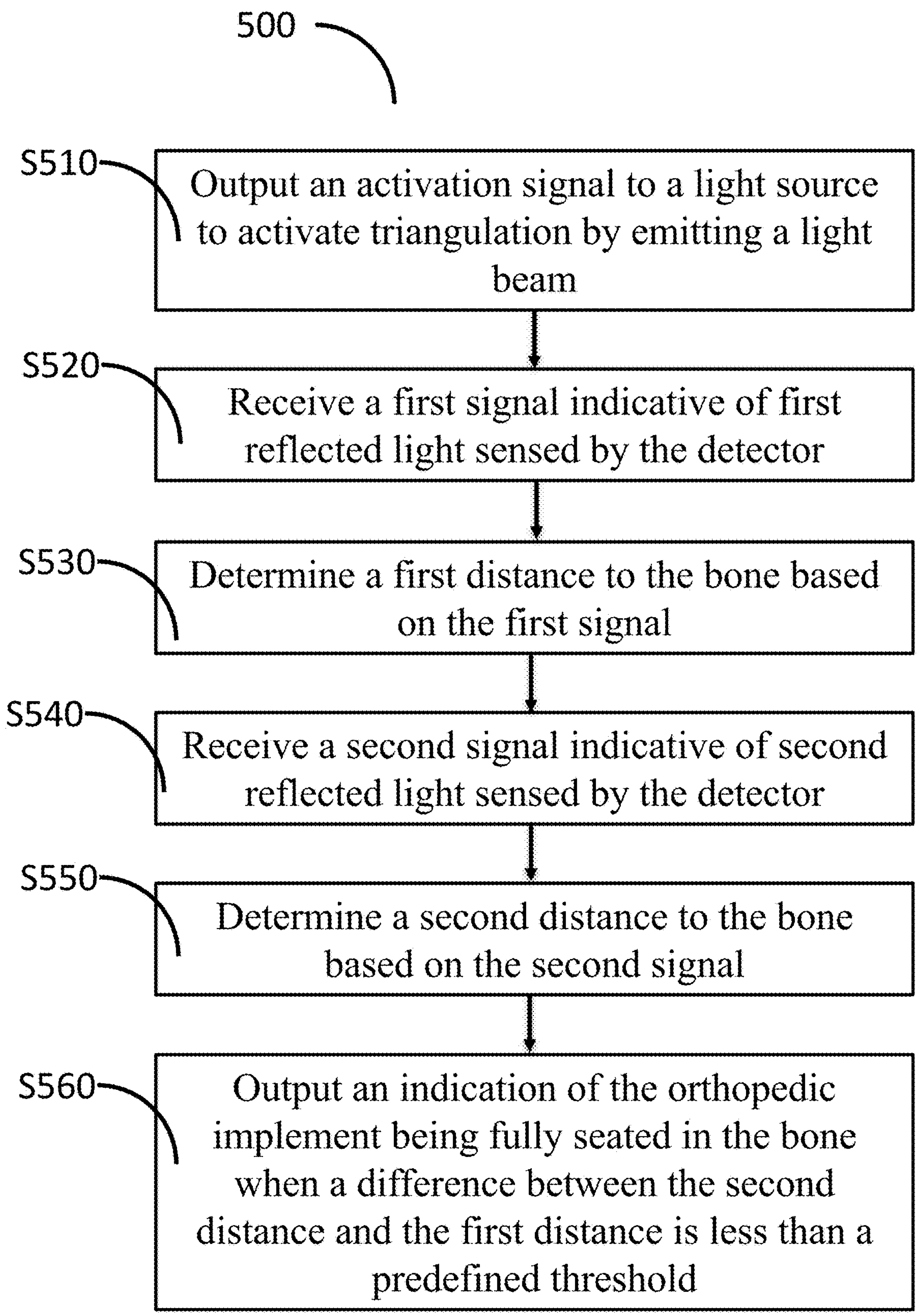
FIG. 5 is a flow chart of a method of determining seating of an orthopedic implement relative to a bone.

For example, as shown in FIG. 5, one or more processors 60, 80 may execute one or more operations based on instructions stored in memory. The one or more operations cause the one or more processors 60, 80 to perform a method 500 including: outputting an activation signal to a light source to activate triangulation by emitting a light beam at block S510; receive a first signal indicative of first reflected light sensed by the detector at block S520; determine a first distance to the bone based on the first signal at block S530; receive a second signal indicative of second reflected light sensed by the detector at block S540; determine a second distance to the bone based on the second signal at block S550; and output an indication of the orthopedic implement being fully seated in the bone when a difference between the second distance and the first distance is less than a predefined threshold at block S560. The method may be performed by any of the embodiments described herein, for example any of the embodiments of FIG. 1-3 or the embodiments in the detailed description.

Further, in some embodiments, as shown in FIG. 1A, the device 30 further includes an optional sensor 94 (e.g., image sensor, camera, or the like) for establishing a presence or absence of cracks, even hairline cracks, in the proximal area of the bone (e.g., femur and/or cortical rim). Additionally, the sensor 94 may transmit one or more images or videos of the presence or absence of cracks to one or more processors 60, 80 to be stored in memory. In some embodiments, as shown in FIG. 1B, sensor 107 may further include auto focus functionality. By experiment, it has been found that a sensor 107 with an about 2-megapixel resolution gives grainy or pixilated images. In some embodiments, device 100 includes a sensor 107 employing a resolution of greater than or equal to about 5 megapixels. The goal of the sensor 107 is to notify a user, surgeon, and/or hospital that no hairline cracks or cracks, in general, are present. Utilizing video or image capture in the software memorializes the image for the patient record.

FIGS. 1B-1C show a device 100 for monitoring the press fit of an orthopedic implement 112 (e.g., stem) into a bone 101 (e.g., a femur, humerus, or the like). Device 100 include a clamp 110 and a clamp friction ring 104 for securing the device 100 to a trunnion 102 of the orthopedic implement 112 by a fastener 103. In some embodiments, the fastener includes a screw (e.g., a socket head screw) that is secured by a key (e.g., hex Key). The clamp 110 may also be secured on the opposite side 120 for surgeon convenience. Fasteners of various sizes may be employed, such that securing the clamp 110 is not limited to the fastener as described above. Various attachment means include screws with fast threads, double lead, power, Acme, and other thread profiles. Various thread angles (fast ramp) and thread profiles can be used to secure the clamp in less than a ½ turn or ¼ turn or better.

In some embodiments, instead of a Hex Key, an upright lever, or a knob can be employed to turn the fastener.

In some embodiments, device 100 is subject to extreme forces by the action of a surgical mallet. These forces can reach upwards of about 7,500 Newtons. By experiment, it has been determined that the clamp friction ring absorbs a lot of the forces; however, the fasteners still tend to loosen. The optional addition of an internal star washer, exterior star washer, locking ring, or other locking device can secure the fastener from repeated mallet impacts that can reach as many as 30 strikes. In addition, an optional upright lever or other device to secure the screw can be locked with a detent, ratchet, or similar component as the screw with an internal star washer, exterior star washer, or locking ring.

The clamp friction ring 104, in some embodiments, has a hardness of about 60 Shore A to about 120 Shore A and includes or is formed of one or more of: silicone, thermoplastic rubber (TPR), thermoplastic net-shaping (TPN), a fluoropolymer elastomer and synthetic rubber compound (e.g., Viton®), polyurethane, ethylene propylene diene monomer (EPDM), polychloroprene (e.g., Neoprene®), or any rubber including a variety of thermoplastic rubbers. A harder rubber tends to "grab" the trunnion 111 allowing the clamp to be secured without movement. A softer rubber below about 60 Shore A and especially at about 40 Shore A has a tendency to continue to compress and creep and not "grab" the trunnion 111 as the clamp closes. A gap in the ring allows the clamp to close. The gap can be large enough to allow movement of the ring around the trunnion.

Trunnions, as in trunnion 102, can have a reverse taper. Employing a lip on the bottom side of the internal diameter of the friction ring 104 can serve to further capture and lock in the trunnion 102.

The clamp 110 can be made of, formed of, or otherwise include acrylonitrile butadiene styrene (ABS), hard anodized aluminum, surgical grade stainless steel, polycarbonate, polyetheretherketone (PEEK), polysulphone, or any engineered plastic. Finite Element Analysis for injection molded parts can be employed to further establish the strength and/or flexibility of the clamp.

In some embodiments, device 100 further includes an adjustment region. For example, the adjustment region may include a hinge, a ball detent, or similar mechanism that allows manipulation of the light source along a z-axis. As shown in FIGS. 1B-1C, in some embodiments, the adjustment region includes a hinge 105. A hinge 105 allows for adjustment of the device 100 such that the sensor 107 is trained on the proximal side of the target location 108 of the bone (e.g., femur cortical rim). Most cracks and hairline cracks occur at this location when the orthopedic implement 112 is pressed in the femur 101. In some embodiments, device 100 is adjustable via a combination of the hinge 105 in the z-direction and the rotation of the clamp 110 in the x-y plane, such that the device 100 can be trained on the target location 108 of the bone. Further, the rotation of the clamp 110 also provides sufficient rotational adjustment to center the sensor 107 on the proximal region of the target location 108. In some embodiments, the target location is a long cortical bone with a rim when cut or machined. In some embodiments, the target location of the bone is a femur cortical rim.

In other embodiments, device 100 does not include one or more hinges, such that the device 100 has an increased height of the sensor and/or light source. By increasing the height from about 1 cm to about 5 cm or about 5 cm to about 10 cm, the use of one or more hinges can be eliminated. It is also possible to employ multiple hinges with increased height of the sensor and laser as well.

One additional method along with a sensor or independent of a sensor includes the use of a methylene blue solution. By brushing or wiping the bone surface (e.g., cortical surface) with a solution of methylene powder or liquid and about 60% to about 90% isopropyl alcohol in a ratio of about 0.5 to about 1; about 1 to about 1; about 1 to about 2; or up to about 1 to about 20, the alcohol and methylene blue serves to reduce the surface tension and thus the contact angle. The bone surface is now more easily "wettable," and the solution more easily seeks and infiltrates a hairline crack which is not normally visible with an unaided eye or X-ray. Further, the blue color provides a stark contrast to the background and improves visibility. The dilute methylene blue solution is now easily removed from the surface with a second brush and only a hairline crack or crack may retain the dilute methylene blue solution. An embodiment may include two brushes or sponge applicators tied together with one containing a dilute methyl blue solution and the other sponge/brush without solution used to remove excess solution from the surface. For example, the dual-applicator system can include one motion or step to expose the crack.

In some embodiments, the use of a 5-megapixel sensor module may provide sufficient resolution when a methylene blue solution may not be used or used to visualize the crack that is enhanced visually with a methylene blue solution. In some instances, the sensor may not autofocus properly unless it is at least about 5 cm from the object. This is especially true with a smaller sensor that has a smaller footprint, for example 8 mm×8 mm. This may additionally include one or more optics to change the focal length or working distance of the sensor. It has been found with some optics that reducing the focal length increases magnification. For example, 2× and greater may be sufficient to see hairline cracks and a methylene blue solution may improve visualization. Further, the sensor may have a field of view of about 60 degrees to about 120 degrees. By raising the height of the sensor from a target location on the bone, more of the surface can be visible. This solves two problems: more of the surface can be visible (i.e., larger distance of the subtended angle due to the increased height); and the image may not be out of focus because the autofocus may also work better because of the increased height.

Thermographic sensors may also be employed to visualize cracks. For example, a FLIR TF40 or other commercial camera can be employed in tandem with a cold solution spread over the bone surface (e.g., cortical rim area). The thermographic sensor may use a gray scale. The cold solution may include sterile water or about 60% to about 90% alcohol. Applying a cold solution to the area may create an immediate "blush" which can obscure the crack. Minimizing the "blush" can be accomplished with a software routine or by wiping excess solution from the area. The water may be mixed with the alcohol or the use of alcohol by itself, as well, to reduce the surface tension and thus wet the surface, for example the crack area.

In some embodiments, the incision for hip surgery is about 8 cm to about 15 cm. A device 100 may be sufficiently small to fit in the incision; however, height is less restricted. See FIG. 3 for insight into the spatial relationship of the device 100 with the incision 105. In some embodiments, a target location of a bone can be in the line of sight of a sensor. In some embodiments, a sensor of any of the devices described herein is at a distance from the target location of less than or equal to about 150 mm. In some embodiments, when the distance between the sensor and the target location is increased, the sensor may be more susceptible to operating room light glare despite optionally employing polarized and/or blue filters.

Figure 2A:
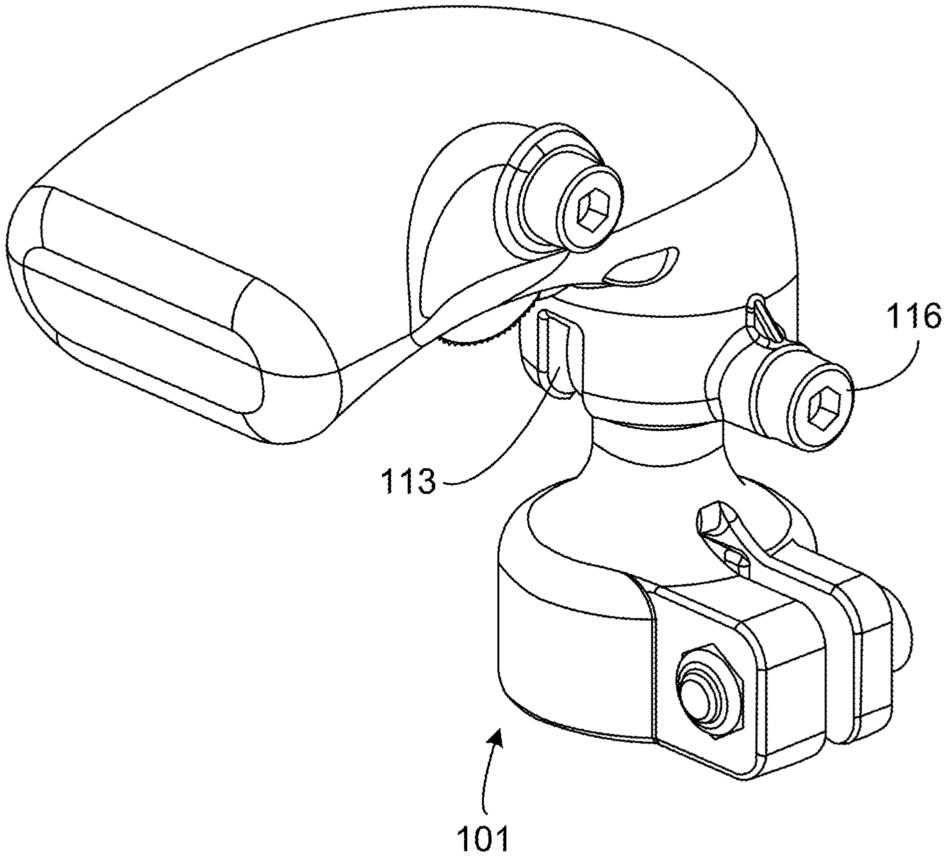
FIGS. 2A-2B show an embodiment of a device for monitoring fixation and stabilization during impaction of an orthopedic implement into a bone.
Figure 2B:
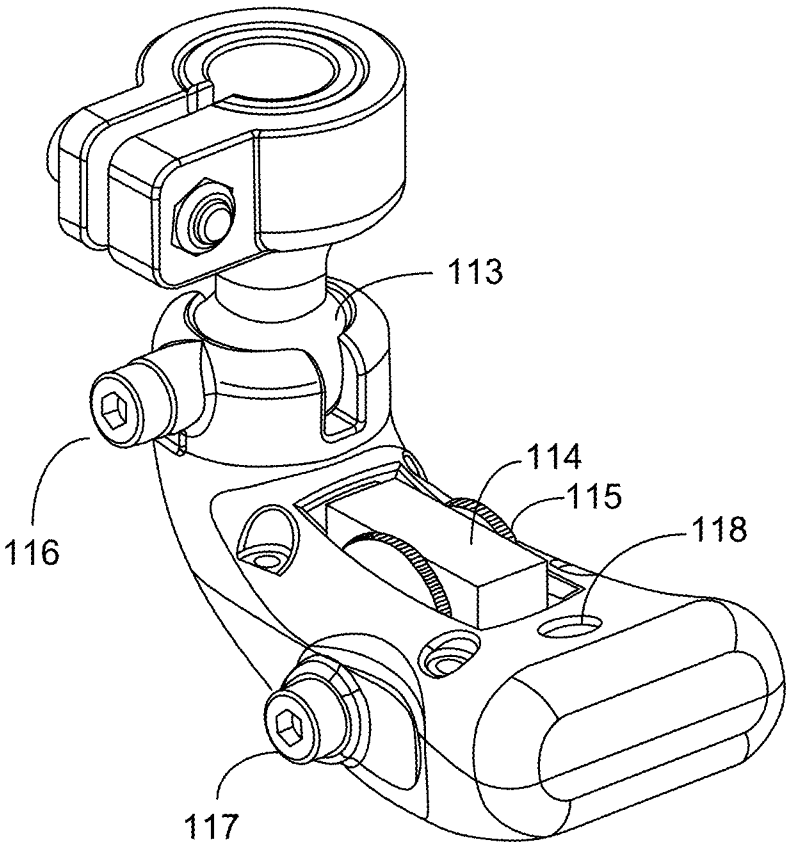
Figure 3:
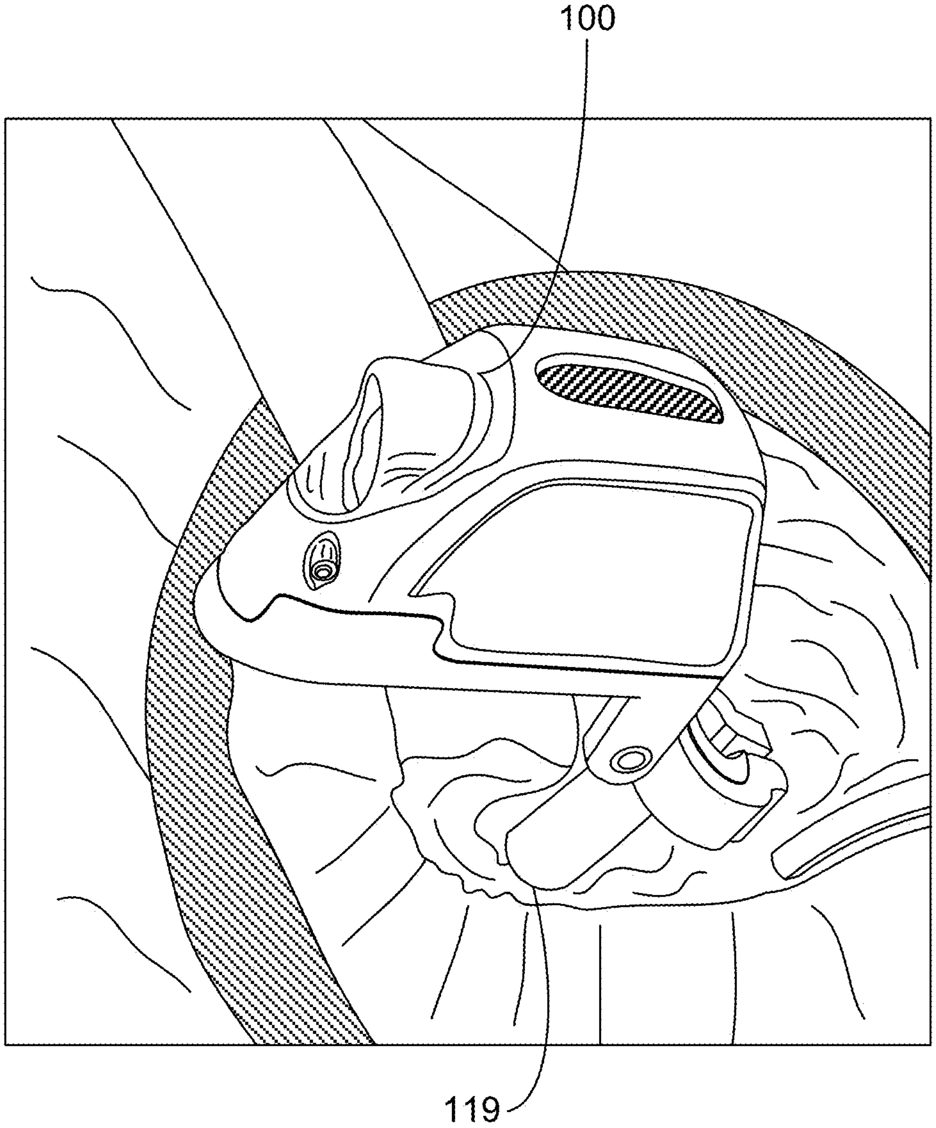
FIG. 3 shows an embodiment of a device situated on a stem in a cadaver study to analyze the space available.

In FIGS. 2A-2B, another embodiment of a device 101 is shown, utilizing laser 114 and sensor 118. In order to improve positioning of the sensor 118 in a middle region of the proximal cortical rim 108, an adjustment region, such as ball detent 113, is employed. The ball detent 113 provides three degrees of freedom compared to device 100 with two degrees of freedom. The additional degree of freedom includes rotation of the ball detent 113 about the z-axis. The ball detent 113 can be secured with fastener 116. Other means of securing the ball detent 113 include an upright lever or a thin knob. The laser 114 can also be adjusted with thumbwheel 115 and then secured with a fastener 117, as shown in FIG. 2B.

In some embodiments, any of devices 30, 100, 101 may further include an optional housing 32 such that one or more components are at least partially positioned in the housing 32. For example, the detector 50 and light source 40 may at least be partially positioned in the optional housing 32.

In some embodiments, a power cable is used to connect to a power source (e.g., 12 V DC) and a connector (e.g., USB cable) can be used for the sensor and optionally communicatively couples to an optional computing device 70. Although a wired connection is shown, one of skill in the art may appreciate that a wireless connection may also be used between various components of the device and/or system. In some embodiments, in any of devices 30, 100, 101, the light source (e.g., laser 105) can connect to an I/O box including a programmable logic controller (PLC) system, which provides the instructions for displaying data on an optional display 90 of an optional computing device 70. In any of devices 30, 100 101, a data cable can connect to an I/O box and optionally to an optional computing device 70.

Figure 4:
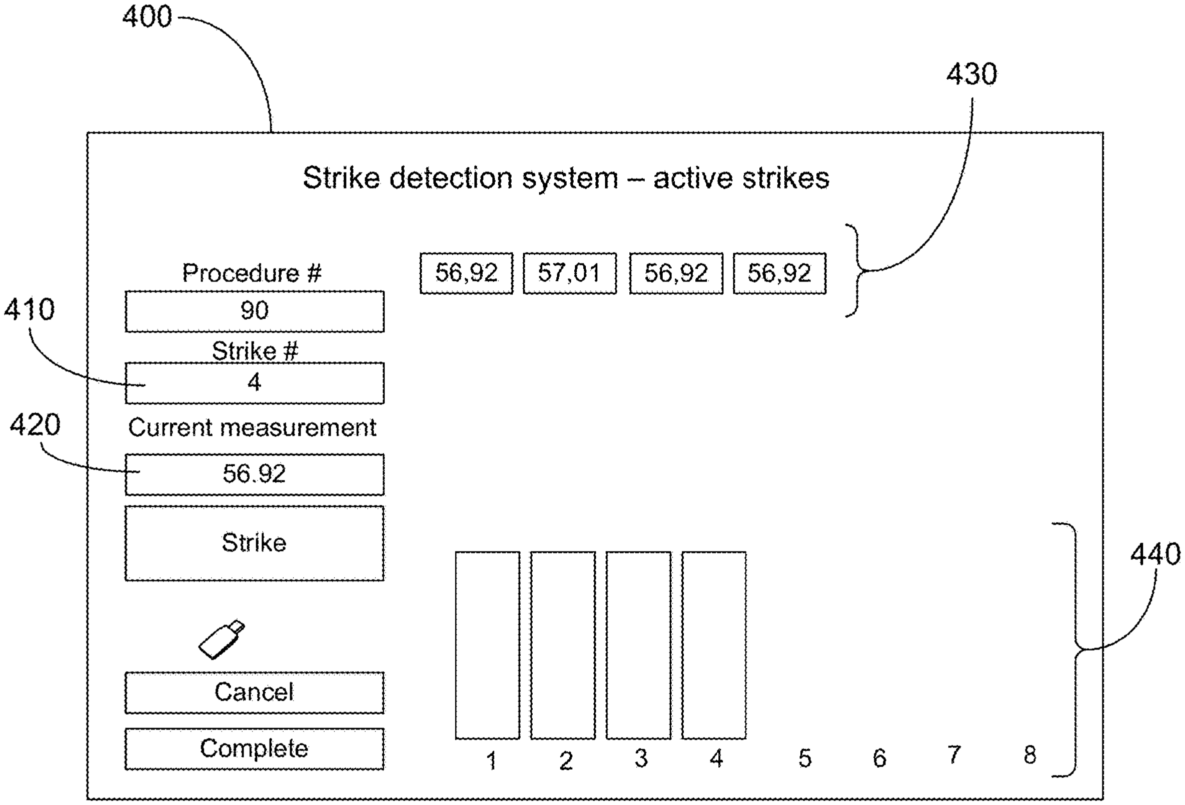
FIG. 4 show a representative user interface that a user may use to check for orthopedic implement fixation.

FIG. 4 shows an example embodiment of a user interface 400 that may be optionally presented on optional display 90 or optional display 96. Optional user interface 400 may optionally display one or more of: a number of strikes 410 (e.g., force applied by surgeon), a current distance measurement 420, one or more previous distance measurements 430, a schematic 440 showing one or more distance measurements, and the like. As described elsewhere herein, optional user interface 400 may be displayed on optional display 96 of device 30 and/or optional display 90 of an optional computing device 70.

In some embodiments, one or more of the devices 30, 100, 101 described herein may include an integrated printed circuit board that may include an analog to digital converter for the light source output and a wireless communication module (e.g., Bluetooth) for the sensor and/or laser. A rechargeable power source (e.g., Lithium battery) may provide power. The light source 40 may be reusable, and the remainder of the device 30, 100, 101 may disposable, such that it is packaged sterile, ready to use one time. Alternatively, the light source 40 and/or device 30, 100, 101 may be draped or otherwise segmented from the sterile field for repeated use.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processor in the triangulation device and/or computing device. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for monitoring a press fit of an implement into a bone, the device comprising:

a light source configured to face a bone configured to receive the implement, wherein the light source is configured to emit a light beam that is reflected by a surface of the bone;

a detector configured to receive the reflected light; and a processor communicatively coupled to the light source and the detector; and a memory coupled to the processor, wherein the memory is configured to store program instructions that, when executed by the processor, cause the processor to perform a method comprising:

outputting an activation signal to the light source to activate triangulation by emitting a light beam, receiving a first signal indicative of first reflected light sensed by the detector, determining a first distance to the bone based on the first signal, receiving a second signal indicative of second reflected light sensed by the detector, determining a second distance to the bone based on the second signal, and outputting an indication of the implement being fully seated in the bone when a difference between the second distance and the first distance is less than a predefined threshold.

2. The device of claim 1, wherein the implement is an orthopedic implement.

3. The device of claim 2, wherein the orthopedic implement is one of: a stem, a broach, an implant, or an insert.

4. The device of claim 1, further comprising a housing configured to at least partially contain the light source and the detector.

5. The device of claim 4, wherein the housing defines a window through which the light beam, from the light source emanates.

6. The device of claim 4, wherein the housing defines a window through which the reflected light is received to interact with the detector.

7. The device of claim 4, further comprising a clamp extending from the housing and configured to secure the housing to a trunnion of an orthopedic implement.

8. The device of claim 7, wherein the clamp is configured to adjust a position of the housing in an x-y plane.

9. The device of claim 7, further comprising an adjustment region between the housing and the clamp, wherein the adjustment region is configured to adjust the position of the housing.

10. The device of claim 9, wherein the adjustment region is configured to adjust the position of the housing along a z-axis.

11. The device of claim 9, wherein the adjustment region comprises a hinge region between the housing and the clamp.

12. The device of claim 9, wherein the adjustment region comprises a ball detent between the housing and the clamp.

13. The device of claim 1, further comprising an image sensor configured to capture an image of a crack in the bone.

14. The device of claim 7, further comprising a friction ring within the clamp, such that the clamp is further configured to be secured to the trunnion of the orthopedic implement.

15. The device of claim 1, further comprising a display, such that the indication is provided as output to the display.

16. The device of claim 1, wherein the bone is a femur or a humerus.

17. The device of claim 1, wherein the processor is communicatively coupled to a display, such that the indication is provided as output to the display.

* * * * *